(12) United States Patent
Grudin et al.

(10) Patent No.: US 11,937,914 B2
(45) Date of Patent: Mar. 26, 2024

(54) METHOD AND APPARATUS FOR MEASURING AIRWAY RESISTANCE

(71) Applicant: SPIRO-TECH MEDICAL INC., Montreal (CA)

(72) Inventors: Oleg Grudin, Montreal (CA); Ronald Jean Dandurand, Beaconsfield (CA)

(73) Assignee: THORASYS THORACIC MEDICAL SYSTEMS INC., Montréal (CA)

( * ) Notice: Subject to any disclaimer, the term of this patent is extended or adjusted under 35 U.S.C. 154(b) by 0 days.

(21) Appl. No.: 17/441,762

(22) PCT Filed: Mar. 27, 2020

(86) PCT No.: PCT/CA2020/050405
§ 371 (c)(1),
(2) Date: Sep. 22, 2021

(87) PCT Pub. No.: WO2020/191499
PCT Pub. Date: Oct. 1, 2020

(65) Prior Publication Data
US 2022/0087569 A1  Mar. 24, 2022

Related U.S. Application Data

(60) Provisional application No. 62/824,393, filed on Mar. 27, 2019.

(51) Int. Cl.
*A61B 5/087* (2006.01)
*A61B 5/085* (2006.01)
*A61B 5/00* (2006.01)

(52) U.S. Cl.
CPC .............. *A61B 5/087* (2013.01); *A61B 5/085* (2013.01); *A61B 5/002* (2013.01); *A61B 5/7221* (2013.01); *A61B 2562/0247* (2013.01)

(58) Field of Classification Search
None
See application file for complete search history.

(56) References Cited

U.S. PATENT DOCUMENTS 3,848,584 A * 11/1974 Otsap ..................... A61B 5/097
                                                                73/239
4,206,644 A *  6/1980 Platt .......................... G01F 1/28
                                                               250/231.19

(Continued)

FOREIGN PATENT DOCUMENTS

CA        3004445 A1    5/2015
CN       101427328 A    5/2009

(Continued)

OTHER PUBLICATIONS

International application No. PCT/CA2014/051073 International Preliminary Report on Patentability Chapter II dated Sep. 15, 2015.

(Continued)

*Primary Examiner* — Michael R Bloch (57) ABSTRACT

A device for measuring lung function parameters using quiet exhalation has a flow tube with a mouthpiece end and an outlet, a shutter covering the outlet of the flow tube, a controllable latch closing and releasing the shutter, a flow sensor for measuring flow in the flow tube following release of the shutter, a pressure sensor for measuring pressure in the flow tube prior to the release of the shutter, a latch controller connected to the pressure sensor and the controllable latch, and a check valve arranged in the flow tube or the shutter for allowing inhalation while the shutter is closed so that the device can be used throughout at least one inhalation and exhalation cycle.

18 Claims, 8 Drawing Sheets

(56) References Cited

U.S. PATENT DOCUMENTS

| | | | |
|---|---|---|---|
| 4,259,967 | A | 4/1981 | Vooren et al. |
| 4,456,016 | A * | 6/1984 | Nowacki .............. A61B 5/0876 137/103 |
| 4,802,492 | A | 2/1989 | Grunstein |
| 5,233,998 | A | 8/1993 | Chowienczyk et al. |
| 5,314,690 | A | 5/1994 | Patterson et al. |
| 5,634,471 | A * | 6/1997 | Fairfax ................ A61B 5/0871 600/538 |
| 5,763,792 | A | 6/1998 | Kullik |
| 6,631,716 | B1 | 10/2003 | Robinson et al. |
| 6,718,975 | B2 | 4/2004 | Blomberg |
| 2003/0100843 | A1 | 5/2003 | Hoffman |
| 2003/0140925 | A1 | 7/2003 | Sapienza et al. |
| 2004/0230108 | A1 | 11/2004 | Melker et al. |
| 2008/0139956 | A1 | 6/2008 | Diong |
| 2008/0178880 | A1 | 7/2008 | Christopher et al. |
| 2009/0312661 | A1 * | 12/2009 | Kullik ................. A61M 16/022 600/538 |
| 2010/0286548 | A1 * | 11/2010 | Lazar ..................... A61B 5/097 600/538 |
| 2011/0282228 | A1 * | 11/2011 | Shiner .................... A61B 5/087 600/534 |
| 2012/0161256 | A1 | 6/2012 | Grudin et al. |
| 2014/0276173 | A1 | 9/2014 | Banner et al. |
| 2015/0258370 | A1 * | 9/2015 | Arkush .................. A61B 5/087 482/8 |
| 2016/0128863 | A1 * | 5/2016 | Loomas .............. A61M 15/002 128/848 |
| 2016/0256073 | A1 * | 9/2016 | Grudin ................... A61B 5/085 |
| 2019/0046079 | A1 * | 2/2019 | Reed ................. A61M 15/0021 |

FOREIGN PATENT DOCUMENTS

| | | |
|---|---|---|
| CN | 107185091 A | 9/2017 |
| CN | 107205695 A | 9/2017 |
| GB | 2270470 A | 3/1994 |
| JP | H08-501004 A | 2/1996 |
| JP | H10-094533 A | 4/1998 |
| JP | 2014-534876 A | 12/2014 |
| JP | 2017-029637 A | 2/2017 |
| WO | 2009/013755 A2 | 1/2009 |
| WO | 2015/005958 A1 | 1/2015 |
| WO | 2015/066812 A1 | 5/2015 |

OTHER PUBLICATIONS

International application No. PCT/CA2014/051073 International Search Report dated Feb. 11, 2015.

International application No. PCT/CA2014/051073 Search Strategy dated Feb. 11, 2015.

International application No. PCT/CA2014/051073 Written Opinion of the International Searching Authority dated Feb. 11, 2015.

European application No. 14859763.6 European search report dated May 23, 2018.

European application No. 14859763.6 European search report dated Jun. 25, 2020.

Chinese application No. 201480084526.0 Office Action dated Sep. 17, 2019.

Chinese application No. 201480084526.0 Office Action dated Aug. 19, 2020.

Kapp et al., "The Shape of Maximum Expiratory Flow Volume Curve", Chest, vol. 94, Issue 4, Oct. 1988, pp. 799-806.

Gritti et al., "A new approach to the determination of airway resistance: interrupter technique vs. plethysmograpghy", J. bras. pneumol. vol. 37 No. 1 São Paulo Jan./Feb. 2011: 61-68.

Schmalisch et al., "Differences in tidal breathing between infants with chronic lung diseases and healthy controls", BMC Pediatrics vol. 5, Article No. 36 (2005), Published: Sep. 8, 2005.

Hage et al., "Detection of flow limitation during tidal breathing by the interruptor technique", European Respiratory Journal 1995 8: 1910-1914.

Gappa et al., "Passive respiratory mechanics: the occlusion techniques", European Respiratory Journal 2001 17: 141-148.

Klaas et al., "The opening interruptor a new variant of a technique for measuring repiratory resistance", Eur J Respir Dis, 1982, 63, 449-458.

Ireneusz Jabloński et al, "A complex mathematical model of the respiratory system as a tool for the metrological analysis of the interrupter technique", XIX IMEKO World Congress Fundamental and Applied Metrology Sep. 6-11, 2009, Lisbon, Portugal.

Burns et al., "A novel hypothesis to explain the bronchconstrictor effect of deep inspiration in asthma", Thorax. Feb. 2002; 57(2): 116-119.

Steinberg et al., "The influence of Occlusion Time on Measuring Respiratory Resistance and Compliance in Infants with Bronchiolitis", Pediatric Research vol. 33, pp. 273-277(1993).

International application No. PCT/CA2020/050405 International Preliminary Report on Patentability Chapter II dated Jun. 15, 2021.

International application No. PCT/CA2020/050405 International Search Report dated Jun. 26, 2020.

International application No. PCT/CA2020/050405 Search Strategy dated Jun. 26, 2020.

International application No. PCT/CA2020/050405 Written Opinion of the International Searching Authority dated Jun. 26, 2020.

K. van der Plas, P. Vooren the "opening" interruptor. A new variant of a technique for measuring respiratory resistance. Eur. J. Respir. Dis. 1982 63, 449-458.

Seidenberg J, Masters IB, Hudson I, Olinsky A, Phelan PD. Disturbance in respiratory mechanics in infants with bronchiolitis. Thorax. Aug. 1989;44(8):660-7. doi: 10.1136/thx.44.8.660. PMID: 2799745; PMCID: PMC462002.

Brief translation of Office action dated Aug. 15, 2023 in corresponding Chinese patent application No. 202080024904.1 with the Office action.

Corresponding Canadian patent application No. 3,134,629 Office action dated Sep. 26, 2022.

Corresponding European patent application No. 20777197.3 extended European search report dated Dec. 2, 2022.

Corresponding Canadian patent application No. 3,134,629 Office action dated Mar. 1, 2023.

Corresponding Chinese patent application No. 202080024904.1 Office Action dated Jan. 5, 2024 (Google translation provided).

Corresponding Japanese patent application No. 202080024904.1 Office Action dated Dec. 12, 2023 (Google translation provided).

* cited by examiner

METHOD AND APPARATUS FOR MEASURING AIRWAY RESISTANCE

CROSS-REFERENCE TO RELATED APPLICATIONS

This application claims priority of U.S. provisional patent application Ser. No. 62/824,393 filed on 27 Mar. 2019, the content of which is hereby incorporated by reference.

TECHNICAL FIELD

The present application relates to medical diagnostics and monitoring devices, more particularly to devices that measure respiratory parameters such as airway resistance.

BACKGROUND

Diagnostics of respiratory disease and monitoring of its progression are based on measuring respiratory parameters. One of such medically valuable parameters is airway resistance.

Interrupter or shutter measuring method is one of the techniques of determining airway resistance which requires minimal cooperation of the subject. With this method, the subject breathes through a breathing tube. At certain moment—usually during exhalation, the opening of the breathing tube is briefly closed by a shutter. Within a short period of time (typically about 100-150 ms) after closing, air pressure in the mouth and breathing tube increases to the level which is supposed to correspond alveolar pressure at the moment of air flow interruption. Measured values of air flow just before shutter closing and built-up pressure are used for determination of airway resistance. One variant of the interruption technique known as "opening" interruption method uses a different sequence of measurements. The flow rate is measured not before the interruption of air flow, but shortly after opening of the shutter. In this method, a longer period of interruption provides more complete equilibrium between alveolar and mouth pressure which improves accuracy of airway resistance measurement. In accordance with this method, interruptions are made only during inspiration and in the middle part of the inspiratory phase. Mouth pressure is measured immediately before opening while air flow is averaged during the period of 15-35 ms after opening of the shutter (K. van der Plas, P. Vooren, "The "opening" interruptor. A new variant of a technique for measuring respiratory resistance." Eur. J. Respir. Dis. 1982 63, 449-458).

During breathing maneuver of another variant of interruption technique is described in Applicant's pre-grant US patent publication US 2016/256073 in which the subject starts to breath into the flow tube initially closed by the shutter. Applicant calls this device and technique Relaxed Occlusion Expiration Monitoring (REOM). After built-up pressure exceeds certain threshold, the shutter is opened and flow spike is measured during 100-150 ms following shutter release. Airway resistance of upper and lower airways is determined by analysis of the shape of the flow waveform. Airway resistance measurement can be done after a single exhalation cycle including occlusion stage and short post-occlusion flow spike.

SUMMARY

Applicant has discovered in the case of REOM that there can be some hesitation among users or patients resulting from inhalation without the device mouthpiece being properly placed in the mouth, followed by the action of placing the mouthpiece in the mouth, before beginning of non-forced exhalation. Improvements of this technique are proposed below in present invention.

Switching from single exhalation (with one interruption event) to spontaneous breathing (when interruption occurs multiple times at the beginning of each subsequent exhalation) makes breathing maneuver easier for the subject. The subject can maintain his or her embouchure and continue to breathe in and out in a relaxed or non-forced manner. Spontaneous breathing is more natural than single exhalation when the subject is concentrated on a single trial and involuntarily might try to control his or her exhalation that may result in too fast or too slow occlusion stage and distortions of flow waveform caused by extra efforts different from efforts applied during quite spontaneous breathing.

In the prior art REOM device, the shutter could be hinged or simply fall off from the flow tube. When the shutter is to work in a continuous mode, it will return to an occlusion position. Applicant has found that when the shutter is arranged to provide little impedance following release for the flow measurement in the period of about 200 ms following release the measurement is not affected by the shutter. At that point, if the shutter begins to return during exhalation, any resistance to the exhalation flow need not be a problem. As soon as exhalation stops and inhalation begins, there is plenty of time for the shutter to return to the occlusion position and be latched.

In some embodiments, there is provided a device for measuring lung function parameters using quiet exhalation has a flow tube with a mouthpiece end and an outlet, a shutter covering the outlet of the flow tube, a controllable latch closing and releasing the shutter, a flow sensor for measuring flow in the flow tube following release of the shutter, a pressure sensor for measuring pressure in the flow tube prior to the release of the shutter, a latch controller connected to the pressure sensor and the controllable latch, and a check valve arranged in the flow tube or the shutter for allowing inhalation while the shutter is closed so that the device can be used throughout at least one inhalation and exhalation cycle.

Multiple shutter opening at the beginning of each exhalation can improve accuracy of measurements by:
- acquiring interruption flow/pressure data from multiple interruption events;
- rejecting certain interruption events if forced efforts are detected, or flow waveform is distorted due to vocalization or other artifacts;
- averaging airway resistance measured in multiple interruption events or
- averaging multiple post-occlusion flow waveforms and further calculating airway resistance for averaged flow waveform.

BRIEF DESCRIPTION OF THE DRAWINGS

The invention will be better understood by way of the following detailed description of embodiments of the invention with reference to the appended drawings, in which.

DETAILED DESCRIPTION

Figure 1A:
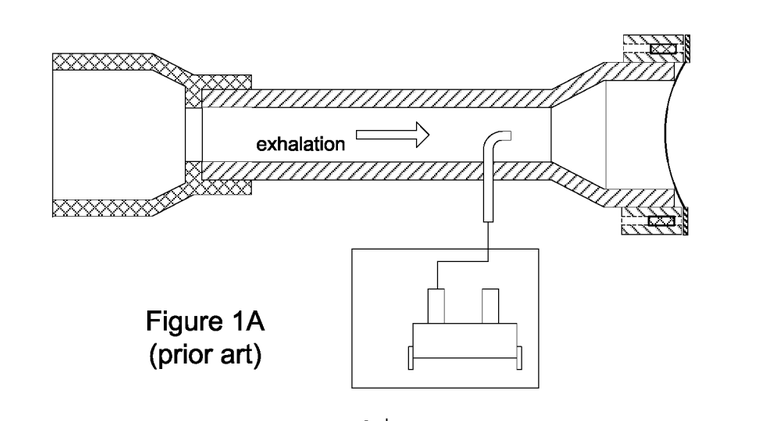
FIG. 1A shows prior art design of the flow tube with shutter for airway resistance measurement using Pitot tube for measuring exhalation flow and a single sensor for measuring both flow and pressure.
Figure 1B:
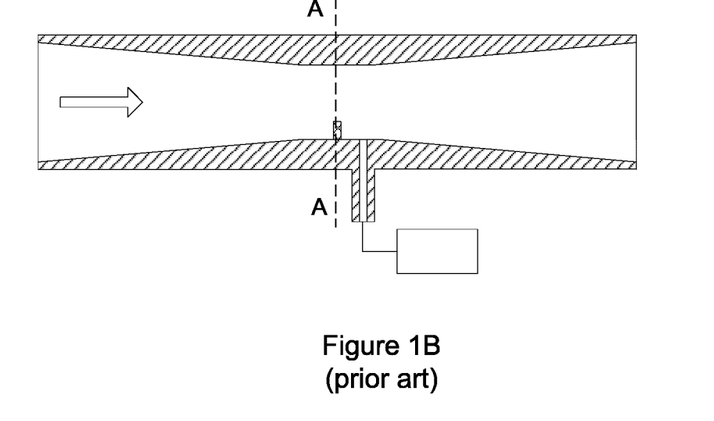
FIG. 1B shows prior art design of the flow tube with shutter for airway resistance measurement using a flow sensor port and baffle arrangement for measuring exhalation flow and a single sensor for measuring both flow and pressure, with the tube cross-section illustrated at the location of the baffle along line A-A in FIG. 1C.
Figure 1C:
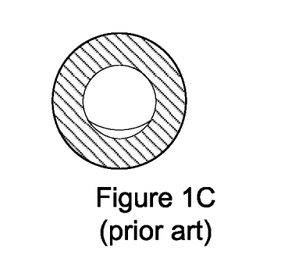

Prior art designs of the flow tube with shutter of the respiratory device for airway resistance measurements are shown on FIG. 1A through 1C. The device performs measurement of airway resistance based on one interruption event at the beginning of a single exhalation. The position of the shutter at the end of post-occlusion spike is not important and undetermined. The shutter can be completely opened or closed. The only requirement is that the shutter stays opened during a first period of about 100-150 ms after shutter release to provide an undistorted flow waveform needed to calculate airway resistance. It will be appreciated however that the shutter does not interfere with the measure of the post-occlusion flow spike.

The transition from an operating mode of the respiratory device based on single interruption event to one based on multiple interruption events at the beginning of subsequent exhalation cycles can provide for an easier, more natural and more convenient breathing maneuver. The subject can breathe spontaneously in a relaxed manner without concentrating on a single exhalation and attempting to control expiratory efforts. Therefore, the results may be more representative of the true lung capacity of the patient.

To implement the operating mode of the respiratory device based on multiple interruption events, the shutter can be structured to provide: a) free unobstructed exhalation immediately after shutter release and during the rest of inhalation, b) blocking of the flow tube at the beginning of exhalation and during occlusion stage. This means that the shutter can be returned to its initial closed position at the beginning of each exhalation.

Figure 2A:
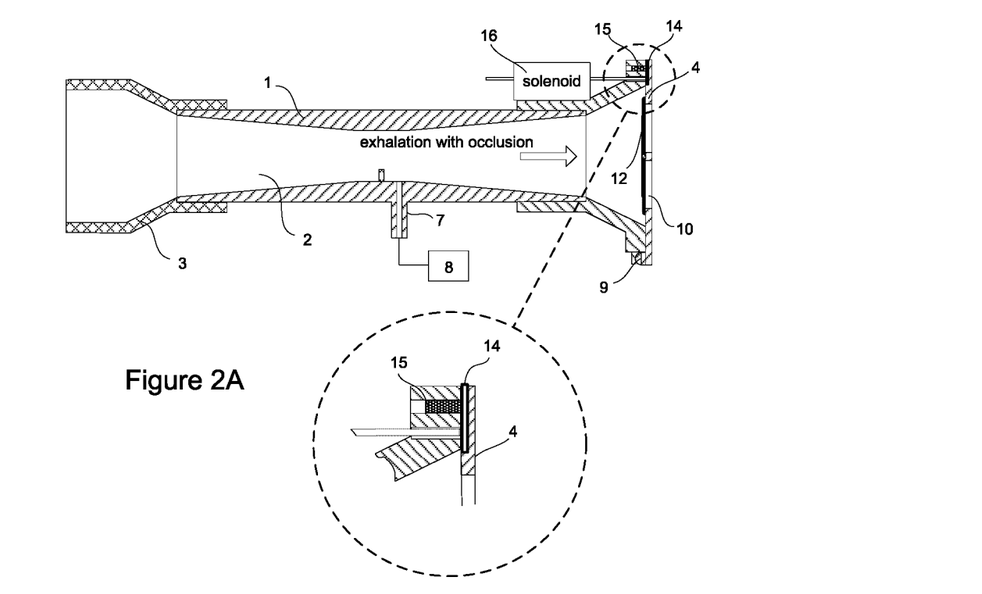
FIG. 2A presents schematically design of the flow tube with the shutter closed at the beginning of exhalation.

FIG. 2A shows one of possible embodiments of the flow tube 1 with the shutter 4. The position of the shutter 4 corresponds to the beginning of exhalation when the flow tube 1 is blocked. The shutter 4 can have one or more openings 10 closed by check valve 12 which can be made from soft and flexible material like rubber or silicone. A magnet 15 can attract a metal fragment 14, such as a ferromagnetic metal clip or insert, of the shutter 4 to prevent opening of the shutter during occlusion when pressure inside the flow tube 1 increases until reaching the desired threshold value. If the shutter 4 is made of a suitable metal material, a separate fragment 14 is not required. Other types of latch mechanisms can be used to hold and release the shutter 4. Flexible check valve film 12 can block the openings 10 in the shutter 4 at this stage. Furthermore, it will be appreciated that the check valve 12 may be replaced by any other means of controlling an opening to allow airflow during an inhalation while preventing airflow during an exhalation, such as using an electronically controlled valve operated based on the sensor reading.

After the built-up pressure exceeds a predetermined threshold, the solenoid 16 can push the shutter 4 to release it from the magnet 15. Increase of distance between the magnet 15 and metal fragment 14 of the shutter 4 reduces magnetic attraction force rapidly, and further shutter 4 opening is done by compressed air accumulated during occlusion stage. When other forms of latch mechanisms are used, different triggers or release mechanisms can be used (e.g. an electromagnet may be used in lieu of the magnet 15 and the release mechanism of the shutter 4 may include de-energizing the electromagnet).

Figure 7:
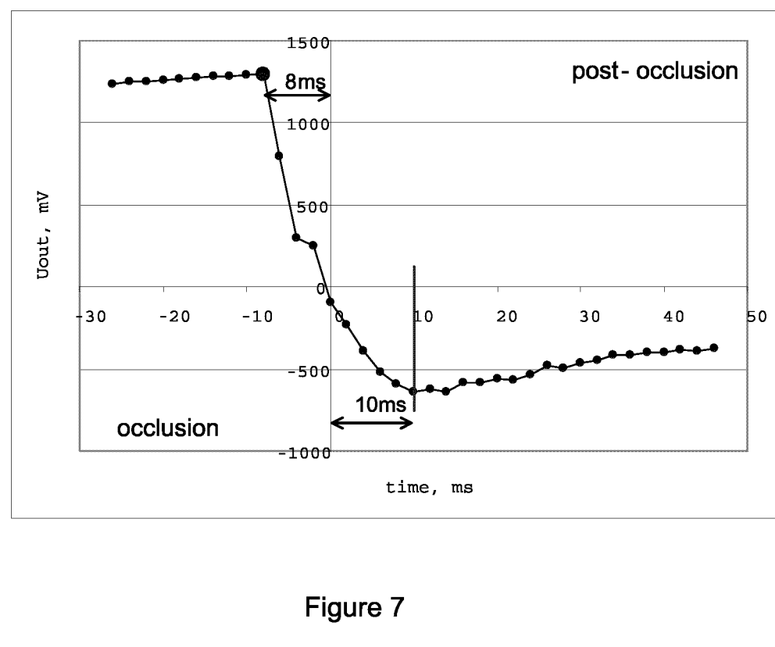
FIG. 7 shows output signal of pressure sensor at the end of occlusion stage and beginning of post-occlusion flow spike after shutter release.

Full opening of the shutter 4 can take about 10 ms with minimal distortions of the air flow. FIG. 7 shows a typical output signal of the sensor 8 measuring pressure in air channel 2 of the flow tube 1. Positive signal corresponds to pressure during occlusion stage (zero flow) while negative signal corresponds to flow after shutter release. It can take approximately 8 ms to open the shutter 4 and reduce built-up pressure to zero. When port 7 is arranged downstream of the baffle, or in a Pitot tube, exhalation air flow through the tube 1 causes negative pressure and negative output signal of the sensor 8. Maximum absolute value of the signal can be reached at about 10 ms after shutter opening and corresponds to peak flow.

The shutter 4, as illustrated, is a single flap-type valve that opens outwardly, thus propelled by and moving with the air flow leaving the flow tube 1. It will be appreciated that more than one flap could be arranged to provide the releasable occlusion at the end of the flow tube 1. The movement of the flap with the release air does not adversely affect the measurement of the flow in tube 1 by sensor 8.

It will be appreciated that the measurement device can comprise circuitry for controlling the latch release, measuring pressure and flow in tube 1 from the sensor 8 15 readings and optionally calculating values such as airway resistance and/or lung compliance from the readings. Such circuitry is described in Applicant's pre-grant patent publication US 2016/256073 (the specification of which is hereby incorporated by reference). For example, this can comprise a microcontroller associated with the sensor 8, and data processing can be done using an associated program or app on a 20 connected device (e.g. Bluetooth®), such as a smartphone or other convenient computing device. This can allow the cost of the data processing to be removed from the measurement device. The recording of such measurements, as described in greater detail below with reference to FIG. 6, can involve collecting measurements over a number of "trials" or exhalations performed as the user breathes in and out 25 normally without forced efforts, and the data can be averaged and/or compiled as desired.

Figure 2B:
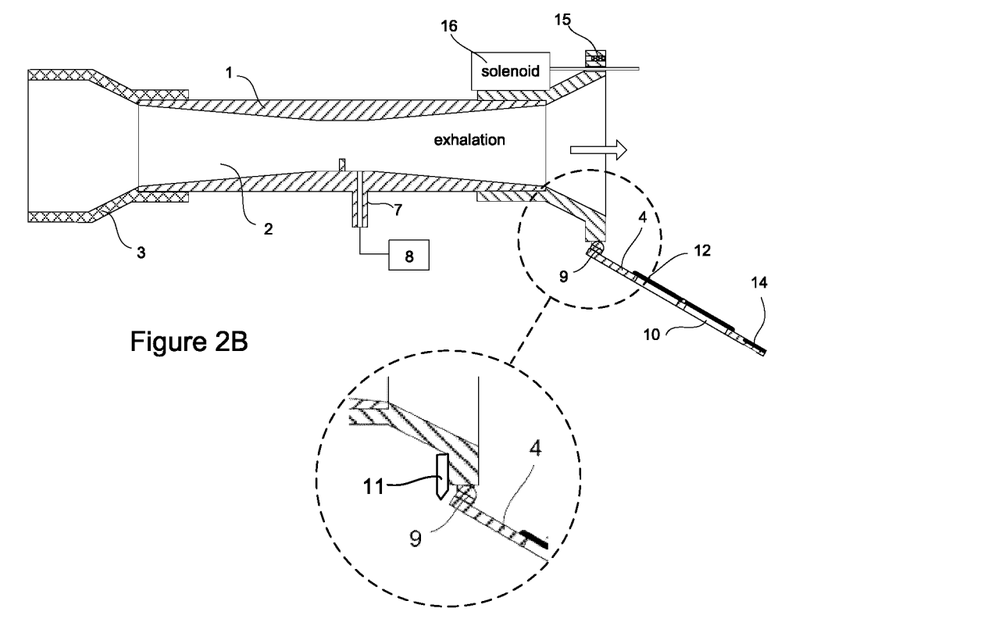
FIG. 2B presents schematically design of the flow tube with the shutter opened during exhalation.

In some embodiments, the method of airway resistance measurement involves measurement of flow in the range of about 100-150 ms after shutter opening. After this time interval, position of the shutter 4 may not be critical for measurements. Preferably, the shutter 4 should not prevent spontaneous exhalation of the subject once it is released. FIG. 2B shows the shutter 4 at the position of maximum opening that can be restricted by a buffer or damper 11. The buffer 11 can provide an abutment for the shutter 4 as it swings open to determine a maximum opening angle of the shutter 4. Opening angle can be an important parameter of the device and will be discussed below. It will be appreciated that the buffer 11 can take a variety of different forms to provide the function of limiting the opening angle.

An external returning force can be applied to the shutter 4 to push it to its initial closed position. This force can be created by a spring or by using electrostatic and magnetic principles. Usage of gravity force is also possible, as demonstrated in the present embodiment. After opening and colliding with the buffer 11, the shutter 4 returns to its initial position and may block the opening of the flow tube 1 preventing normal exhalation of the subject. To exclude this possibility, the solenoid 16 stays powered on to prevent the shutter 4 from touching magnets 15 and leaving a gap between the shutter and the flow tube wide enough for exhalation. The buffer 11 can also, if desired, provide some elastic energy to send the shutter 4 back to the closed position, thus aiding gravity or the spring mechanism, for example.

Start of inhalation can result in significant negative pressure inside the flow tube 1 that can be detected by the sensor 8. Immediately after inhalation is detected, the solenoid 16 can be powered off, and the shutter 4 can stick to the magnet 15 (the latch is closed). Check valve 12 is opened allowing subject to inhale through the flow tube 1. Position of the shutter 4 during inhalation is shown on FIG. 2C.

Figure 2C:
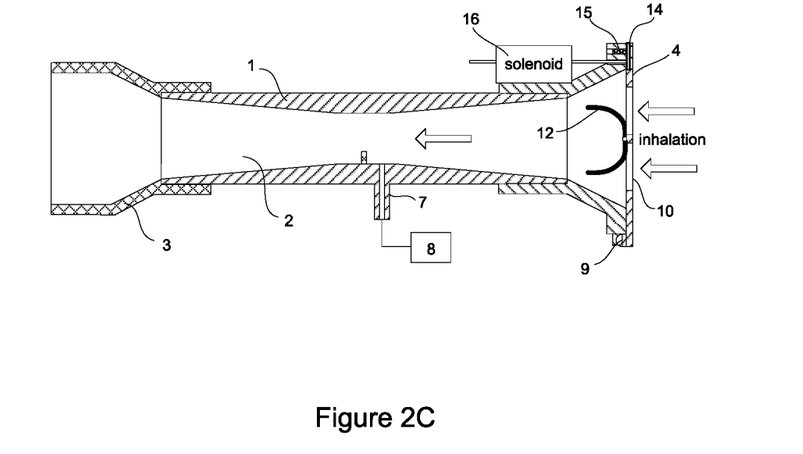
FIG. 2C presents schematically design of the flow tube with the shutter closed during inhalation with a valve opened.

After the subject finishes inhalation and starts to exhale, positive pressure inside the flow tube 1 closes the check valve 12 and a new occlusion stage starts.

Figure 2D:
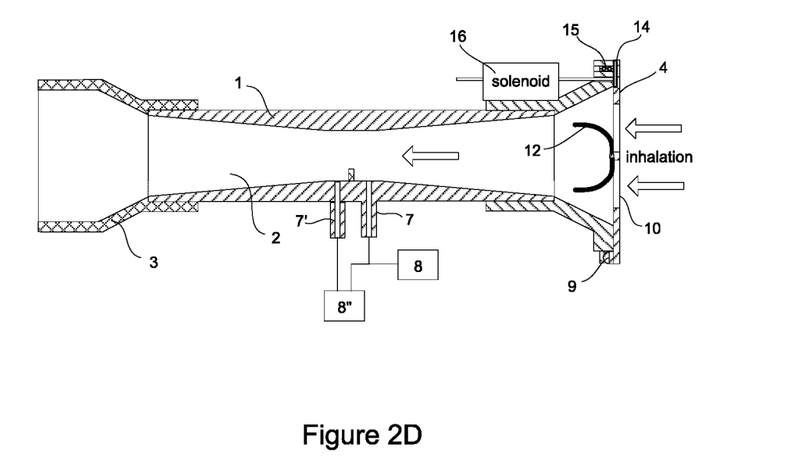
FIG. 2D presents schematically a variant design of the flow tube with the shutter closed during inhalation in which the flow tube has an additional port and sensor for measuring inhalation flow.

FIG. 2D shows an embodiment in which an additional port 7' can be added before the flow baffle positioned before port 7. The port 7' can be located as illustrated so that inhalation flow can be measured using sensor 8". Sensor 8" is illustrated as being connected to measure the differential pressure across the baffle in the flow tube, and sensor 8" will then measure both inhalation and exhalation flows. It will be appreciated that other arrangements for measuring inhalation are possible and that measurement of inhalation is optional if only exhalation flow is of interest. By measuring inhalation flow and exhalation flow over one or more breathing cycles, the device can measure further lung parameters such as tidal volume, slow vital capacity, etc. When measuring slow vital capacity (SVC), the shutter can be kept open, if desired. Various arrangement of flow sensors can be used. A single sensor may be used to measure forward and reverse flows, while another sensor may be used to measure pressure. Measurement of flow/volume parameters of breathing may require fixing shutter 4 in permanently opened position and temporary disabling of airway resistance measurement mode.

Figure 3:
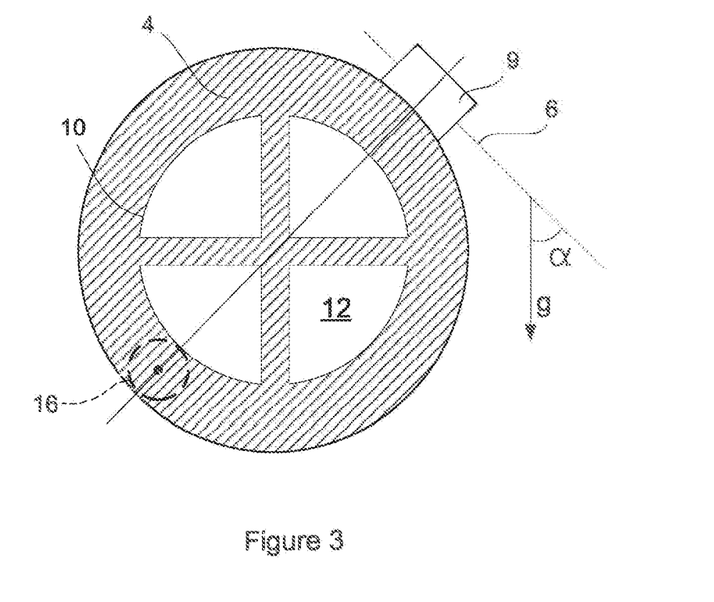
FIG. 3 shows design of the shutter with inclined axis of rotation.

FIG. 3 shows front view of one embodiment in which the shutter 4 with hinge 9 rotates about axis 6 inclined at angle $\alpha$ to the direction of gravity acceleration. Dynamics of the shutter 4 opening and closing can then depend on the following parameters:
  angle $\alpha$;
  mass of the shutter 4:
  position of the buffer 11 which restricts opening angle of the shutter 4.

If there is no hinge, it will be appreciated that the shutter would need to be placed in the closed position before use, however, the check valve will allow a patient to begin use of the device by initially completing quiet inhalation prior to beginning quiet exhalation. The stability of the quiet exhalation and resulting measurement can be improved by beginning the maneuver with inhalation.

In the embodiment of FIG. 3, when performing SVC, it is possible to rotate the flow tube such that gravity keeps the shutter 4 open.

By adjusting these three construction parameters, it is possible to meet the following conditions. The time interval between the shutter opening and its collision with flow tube can exceed the observation time needed to measure post-occlusion flow waveform i.e. about 150 ms. If collision of the shutter with the flow tube occurs faster than the mentioned time, a flow disturbance caused by this collision can disturb the device measurement.

In one particular case of the device embodiment, the damper or buffer 11 can be positioned such that the opening angle of the shutter 4 is about 150°. Angle $\alpha$ between the rotation axis and the direction of gravity acceleration can be chosen to be about 75°. Experimentally measured time interval between shutter opening and its collision with the flow tube is about 250 ms which is long enough to perform undistorted flow waveform measurements to determine airway resistance.

After the user starts to inhale, negative pressure is generated inside the flow tube 1 and can be detected by the sensor 8.

It will be appreciated that the use of gravity to cause the shutter 4 to return towards a closed position can be replaced by or aided by the use of a light spring or biasing member. If gravity or the biasing fails to cause the shutter 4 to seal against the end of the flow tube 1, it will be appreciated that subsequent inhalation will help close the shutter until the check valve 12 opens, and even then, a small negative pressure will be present inside the tube 1 during inhalation that will help keep the shutter 4 closed.

After detection of inhalation, solenoid 16 can be powered off (normally the release mechanism is triggered only momentarily to cause shutter release) and the shutter can stick to the magnets 15. Floppy film of the check valve 12 can bend inwardly due to negative pressure inside the flow tube 1 generated during inhalation and can open the holes 10 in the shutter 4 allowing air to flow through the flow tube 1. The check valve 12 can be opened until the end of the inhalation. When the subject starts exhalation, the check valve 12 is closed and occlusion stage begins.

Figure 4:
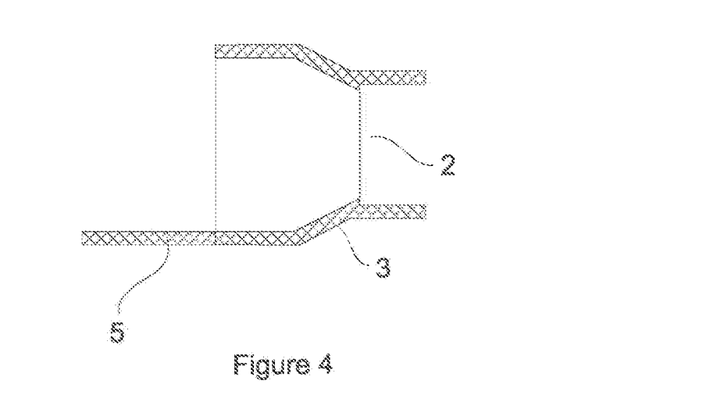
FIG. 4 shows mouthpiece of the flow tube.

FIG. 4 shows an example of the mouthpiece 3 connected to the air channel 2 of the flow tube 1. The mouthpiece 3 contains an optional tongue depressor 5 to fix the position of the tongue preventing it from possibly obstructing opening of the flow tube 1, distort air flow stream and adversely affect measurements of the respiratory device. Such a mouthpiece 3 can be made disposable. It also can be an integral part of the flow tube 1, and the whole flow tube 1 joined with mouthpiece 3 can be made disposable. The mouthpiece 3 can be also integrated with bacteriological filter.

Figure 5A:
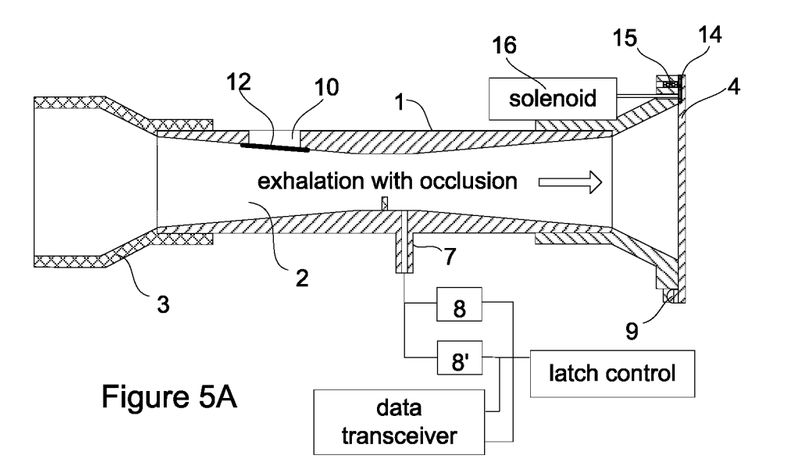
FIG. 5A shows one of the embodiments of the device with alternative position of the valve integrated with the flow tube.

FIG. 5A shows one alternative embodiment of the device where check valve 12 closes an opening 10 in the body of the flow tube 1. In this configuration of the device, there is no need to attach the check valve 12 to the shutter 4 and make holes 10 in the shutter 4.

Also illustrated in FIG. 5A is the option that the sensor 8 can be split into two distinct sensors 8 and 8', for exhalation flow and pressure respectively, instead of using one sensor operative for both flow and pressure. FIG. 5A also illustrates that a latch controller can be included in the device for controlling the release of the latch based on pressure measurements. FIG. 5A also illustrates that the data from the sensor 8 can be transmitted to another device for processing using a data transceiver, such as a wireless link, cable link, etc.

While not illustrated, the external processing device can be used to monitor the pressure during shutter occlusion and to signal latch release. If inhalation flow is also to be measured, the flow sensor 7',8" would need to be arranged at port 10.

Figure 5B:
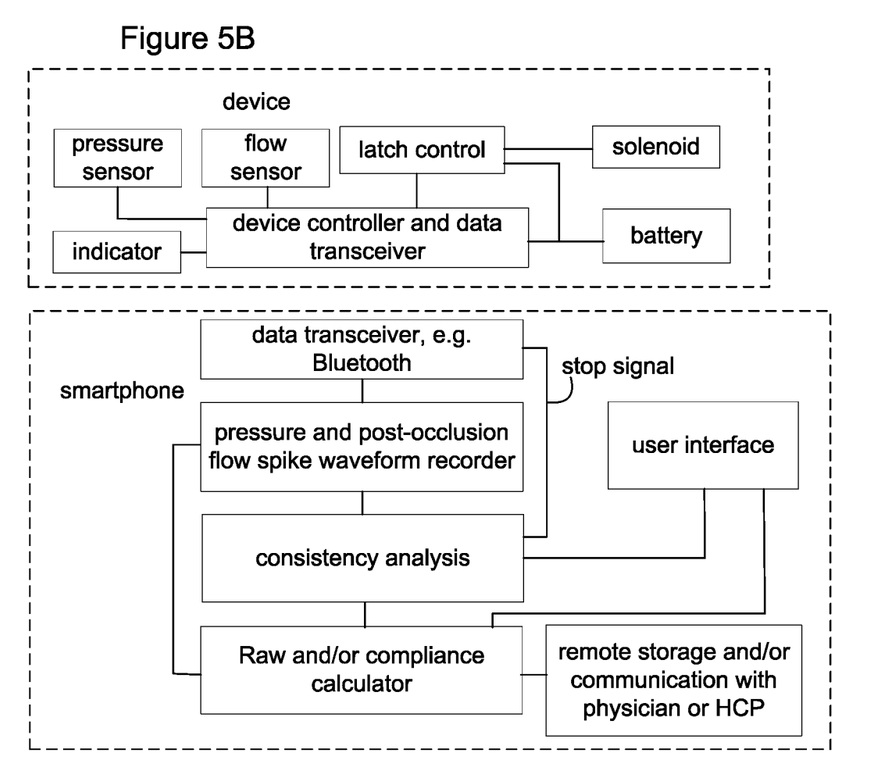
FIG. 5B shows schematic block diagram of one of the embodiments of the device in combination with a smartphone or computing device.

In FIG. 5B, a system is illustrated that comprises the device in combination with a computing device, such as a smartphone. The computing device can comprise a processor, memory storing a computer program for the device 1, a data transceiver for communicating with the device 1, as well as, optionally, a network interface for communicating data and/or receiving settings from a remote party. The device can comprise a microcontroller or microprocessing semiconductor unit that can include the wired or wireless transceiver for communicating with a computing device. Functions such as shutter control, acquisition control using an indicator on the device or a user interface on the computing device, data acquisition and storage, Raw and/or compliance calculation, etc. can therefore be achieved using either the device's processing power or the computing device's processing power as desired.

In the exemplary embodiment of FIG. 5B, the device is configured to control the shutter release based on a pressure threshold, whose value can be set, for example, by the computing device's software and/or the user interface's settings. The computing device can include software for communicating results from the device to a health care professional (HCP), and the shutter release pressure setting can be set by the HCP if desired. Alternatively, the shutter release can be controlled from the computing device, in which case the device transmits the pressure readings every few milliseconds to the computing device.

FIG. 5B also shows that the computing device can perform a flow-spike waveform consistency analysis. This analysis is optional and could also be performed by the device's processor if desired. A consistency analysis can be a comparison of the flow spike waveforms (e.g. the post-occlusion flow data, typically up to about 150 ms after peak flow) with respect to each other. Because a measurement can be taken with every exhalation, it is easy to acquire multiple waveforms. When a waveform is significantly different from the others, perhaps due to a forced effort, cough, vocalization, etc., then that waveform can be disregarded. Measurements can then be done using a number of consistent waveforms and their associated flow tube pressures at the time of the release of occlusion.

Optionally, the device or the smartphone can signal to the user that data acquisition is over, either because a time period or number of exhalations has passed and/or because a number of consistent waveforms has been collected. A stop signal (e.g. audible or visual) can be issued either by an indicator on the device or through the smartphone or computer.

The software in the device or the computer can also be arranged to take a measurement of slow vital capacity. This measurement can begin with the user selecting the measurement or by the device and/or the computer indicating to the user that such measurement is to begin. The user is to inhale slowly and fully, followed by slow exhalation with muscle efforts to fully exhale air from the lungs. The device measures the flow during this exhalation and can record the volume of air in the exhalation as the SVC measurement. If the device measures also inhalation flow, the SVC measurement can involve measuring the volume of inhalation and exhalation to confirm the SVC measurement by using both inhalation and exhalation data. Thus presence of the shutter and its release pressure does not adversely affect the SVC measurement.

While it can be preferred to separate the system between the device and the smartphone as a way to provide a better user interface and to reduce the cost of the device, it will be appreciated that the device can incorporate a user interface and can incorporate network connectivity so that the device can be fully independent of any smartphone or computer.

Figure 6:
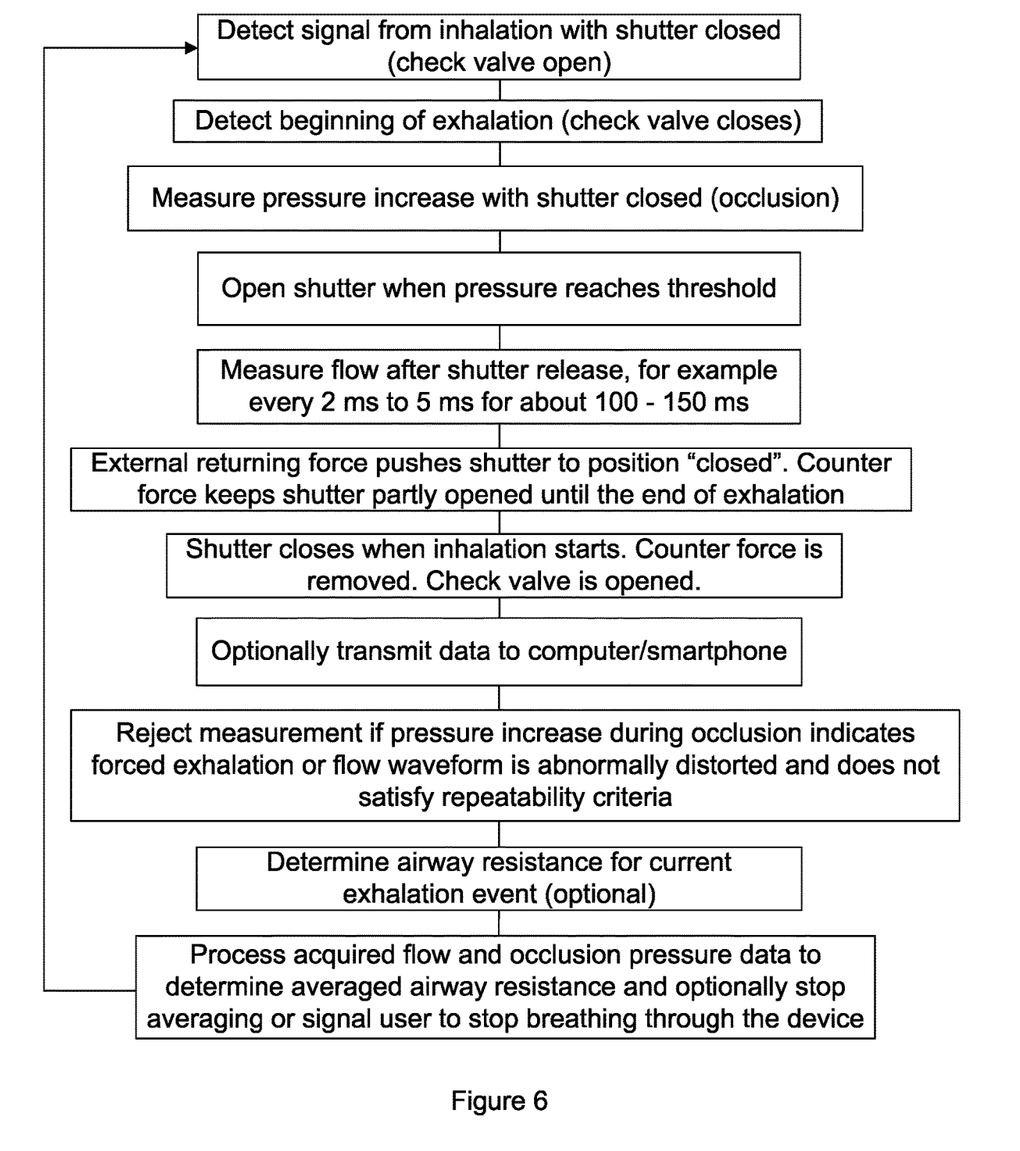
FIG. 6 is a schematic flow diagram describing operation of the device.

FIG. 6 shows block diagram of one possible embodiment explaining the operation of the respiratory device during one breathing cycle.

First the shutter 4 is closed and the check valve 12 is opened when the subject inhales (see FIG. 2C). Transition from inhalation to exhalation is accompanied with a change of pressure inside the flow tube 1, from negative to positive, that can be detected by the sensor 8. The check valve can be closed automatically when exhalation starts.

At the next step, the sensor 8 can measure built-up pressure during the occlusion stage. The solenoid 16 can be powered on when built-up pressure inside the flow tube 1 reaches predetermined threshold value. The solenoid 16 can push the shutter 4 resulting in fast opening of the flow tube 1. As mentioned above, other latch mechanisms may be used without departing from the teachings of this disclosure.

Post-occlusion flow can be measured during a period of about 100-150 ms after shutter 4 release and when the shutter is widely opened. Based on these data, airway resistance can be calculated.

An external returning force can be applied to the shutter 4 after its opening in order to return the shutter to its initial closed position. This force can be created, for example, by a spring or by gravity. Other sources of external returning force like electrostatic or magnetic are also possible. A second force counteracting the returning 10 force prevents complete closing of the shutter 4, such that to the patient may continue exhalation. The second counteracting force can be created, for example, by the solenoid 16. The solenoid 16 continues to be powered on that keeps gap between the shutter and the edge of the flow tube 1. Typically pressure inside the flow tube 1 is positive during exhalation when the shutter is partly closed.

Transition from exhalation to inhalation is accompanied with changing of air pressure inside the flow tube 1 from positive to negative. After such transition is detected, for example by the sensor 8, the counteracting force may be switched off (e.g. powering off solenoid 16) and the shutter 4 can be completely closed by external returning force. The shutter 4 can stick to the magnets 15. Negative pressure inside 20 the flow tube 1 can bend check valve 12 inward resulting in holes 10 opening and allowing air flow through the tube 1 during inhalation.

Calculation of airway resistance and/or lung compliance using the post-occlusion non-forced exhalation flow waveform and occlusion pressure is described in Applicant's pre-grant patent publication US 2016/256073 published 8 Sep. 2016. Measured raw data on interruption event can be (optionally) transmitted to the computer or smartphone at this stage. Alternatively, data can be transmitted continuously during all stages of the breathing cycle if electronic hardware supports such operating mode.

As the computer or smartphone receives measurement data, decision on acceptability of measurements can be done in real time. For example, abnormally short occlusion time can indicate applying of excess exhalation efforts which may not be acceptable during non-forced airway resistance measurements. Distortions of post-occlusion flow spike caused for example by vocalization or other artifacts can be also detected. Such data can be rejected. After execution of several interruption events, averaged flow spike waveform can be calculated. Those flow waveforms which deviate from averaged waveform more than certain percentage and do not satisfy repeatability criteria can be excluded from further analysis.

As one of possible options, airway resistance can be determined for each single interruption event. Then averaged airway resistance can be calculated during execution of multiple interruption events. Alternatively, averaged post-occlusion flow waveform can be calculated with exclusion of single interruption events which do not comply with repeatability criteria. After that, airway resistance can be calculated from the averaged flow waveform.

Measurement procedure can be automatically finished if the desired number of acceptable interruption events was produced and measured.

Figures 8, 9:
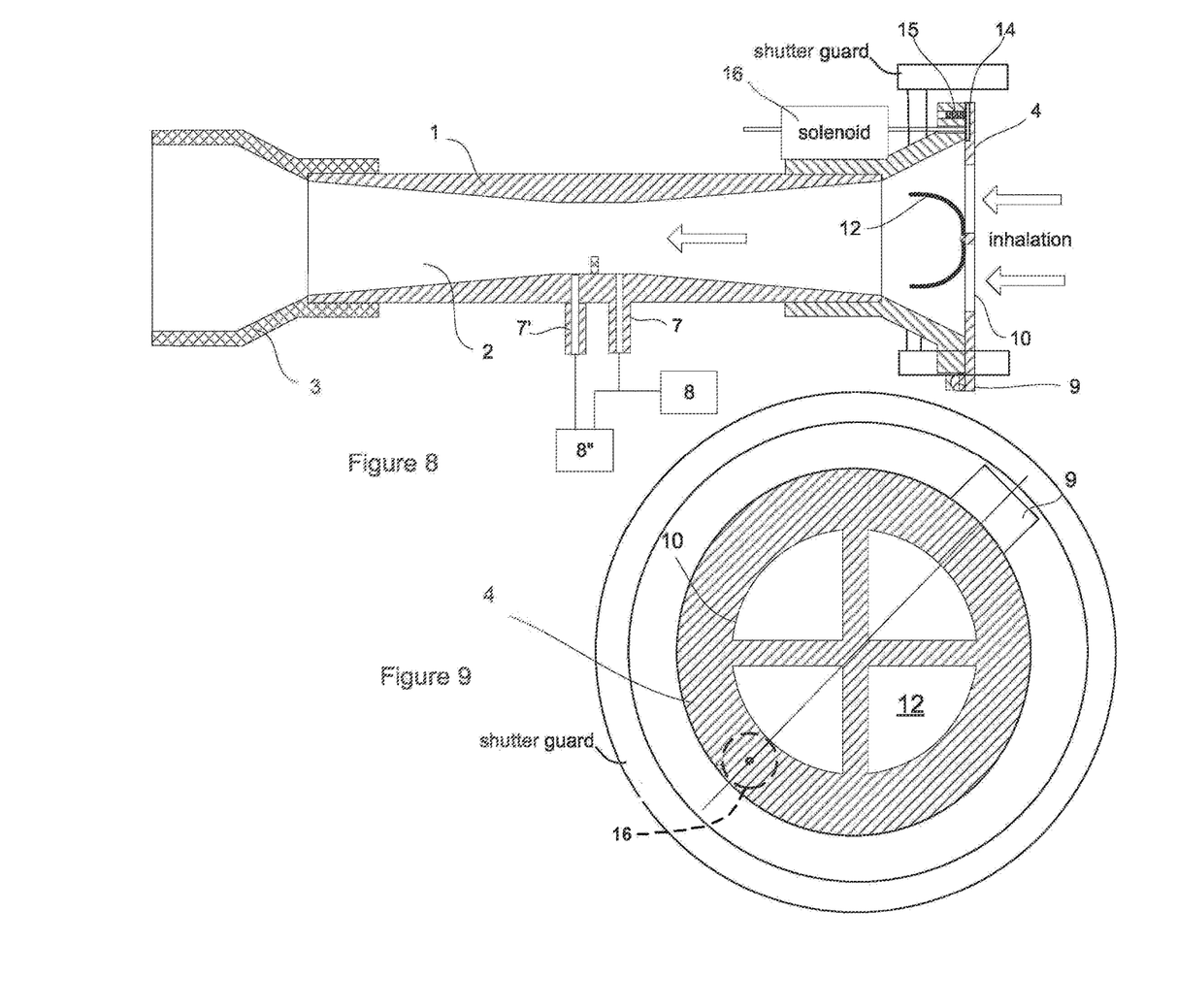
FIG. 8 presents schematically a variant design similar to FIG. 2D of the flow tube with the shutter closed during inhalation in which the flow tube has a shutter guard.
FIG. 9 is a front view of the embodiment of FIG. 8 showing the shutter guard.

The shutter can be made of thin plastic or metal material, and thus can be fragile if knocked open and impacted by a foreign object. In FIGS. 8 and 9, a guard ring is shown as being added at the end of the flow tube that can be used to prevent the shutter from being struck as a result of careless storage. This guard ring is arranged so as to not interfere significantly with the shutter's movement or with the flow of air being expelled from the flow tube. While a ring has been illustrated, it will be appreciated that the shutter guard can take different forms, for example it could comprise a number of projections arranged around the distal end of the flow tube. Such an alternative arrangement can provide an even lower interference with airflow at the distal end of the flow tube. The shutter guard may further be designed to protect the shutter both in its closed and open position.

What is claimed is:

1. A device for measuring lung function parameters comprising:
    a flow tube having a mouthpiece end and an outlet;
    a shutter covering the outlet of the flow tube;
    a hinge connecting the shutter to the flow tube such that said shutter opens outwardly in a manner that is configured to be propelled by and moved with an air flow leaving the flow tube;
    wherein said hinge is mounted on the flow tube with its rotational axis making an angle with respect to gravity acceleration so that gravity causes the shutter to return to a closed position after said shutter opens outwardly with the airflow leaving the flow tube to allow for multiple shutter openings;
    a controllable latch closing and releasing the shutter;
    a flow sensor for measuring flow in the flow tube following release of the shutter, wherein the shutter with a mass and said angle of said hinge are arranged to provide low impedance following release of the shutter for the flow measurement in the flow tube in the period of about 200 ms following release of the shutter, such that the measuring flow in the flow tube is not affected by the shutter;
    a pressure sensor for measuring pressure in the flow tube prior to the release of the shutter;
    a latch controller connected to the pressure sensor and the controllable latch; and
    a check valve arranged in the flow tube or the shutter for allowing inhalation while the shutter is closed so that the device can be used throughout at least one inhalation and exhalation cycle.

2. The device as defined in claim 1, further comprising a calculator connected to said flow sensor and said pressure sensor for calculating the lung function parameter.

3. The device as defined in claim 2, wherein said calculator uses data from said flow sensor for up to about 150 ms from peak flow following the release of the shutter to calculate the lung function parameter.

4. The device as defined in claim 2, wherein said calculator calculates said lung function parameter from multiple interruption events at the beginning of subsequent exhalation cycles.

5. The device as defined in claim 4, wherein the lung function parameter is airway resistance.

6. The device as defined in claim 1, further comprising a data transmitter for transmitting data from said device to a computing device for calculating the lung function parameter from said data.

7. The device as defined in claim 6, wherein said data comprises said flow sensor measurements from peak flow to up to about 150 ms from peak flow following the release of the shutter.

8. The device as defined in claim 1, wherein said flow sensor is configured to additionally measure inhalation flow.

9. The device as defined in claim 1, wherein said flow sensor is a first flow sensor for measuring exhalation, and the device further comprising a second flow sensor for measuring inhalation.

10. The device as defined in claim 1, wherein said latch controller connected to the controllable latch and the pressure sensor is configured to release the shutter at a beginning of exhalation when pressure in the flow tube has begun to increase without forced efforts.

11. The device as defined in claim 1, wherein said latch controller releases the controllable latch at a predetermined pressure.

12. The device as defined in claim 11, wherein said predetermined pressure is defined by an external computing device.

13. The device as defined in claim 1, wherein said check valve is arranged in the shutter.

14. The device as defined in claim 1, wherein exhalation flow is measured for a full exhalation, further comprising a calculator connected to said flow sensor for calculating a slow vital capacity from said full exhalation following the release of the shutter.

15. The device as defined in claim 1, further comprising a shutter guard mounted to a distal end of the flow tube.

16. In combination, the device measuring lung function as defined in claim 1, wherein said device comprises a data transceiver, and a computing device comprising a corresponding data transceiver and memory storing a computer program for communicating with said device and providing a user interface for controlling said device.

17. The combination as defined in claim 16, wherein said computing device further comprises a calculator for calculating a lung function parameter from data from at least one interruption event at the beginning of subsequent exhalation cycles.

18. The device as defined in claim 1, wherein the device further comprises a biasing member assisting the shutter to return towards said closed position.

* * * * *